United States Patent [19]

Tarnai

[11] Patent Number: 4,704,892

[45] Date of Patent: Nov. 10, 1987

[54] CONTROL SPECIMEN FOR EVALUATION OF NON-DESTRUCTIVE TEST RESULTS, ARTIFICIAL INCLUSIONS AND PROCESS FOR PRODUCING CONTROL SPECIMENS

[75] Inventor: György Tarnai, Budapest, Hungary

[73] Assignee: Vasipari Kutato es Fejleszto Vallalat, Budapest, Hungary

[21] Appl. No.: 816,720

[22] Filed: Jan. 7, 1986

[30] Foreign Application Priority Data

Jan. 7, 1985 [HU] Hungary ................................ 43/85

[51] Int. Cl.$^4$ .................... G01D 18/00; G01N 33/20; G01N 29/04
[52] U.S. Cl. .................... 73/1 DV; 73/1 R; 378/207; 324/202; 29/428
[58] Field of Search ............. 73/1 R, 1 DV; 378/207; 324/202; 29/428

[56] References Cited

U.S. PATENT DOCUMENTS

| | | | |
|---|---|---|---|
| 3,677,061 | 7/1972 | Visser | 73/1 DV X |
| 3,933,026 | 1/1976 | Ham et al. | 73/1 DV X |
| 4,028,545 | 6/1977 | Foster | 378/207 |
| 4,173,139 | 11/1979 | Conn | 73/1 DV |
| 4,203,315 | 5/1980 | Vieu et al. | 73/1 DV X |
| 4,238,963 | 12/1980 | Ries et al. | 73/1 R X |
| 4,309,904 | 1/1982 | Jones et al. | 73/1 DV X |
| 4,331,021 | 5/1982 | Lopez et al. | 73/1 DV |
| 4,406,153 | 9/1983 | Ophir et al. | 73/1 DV |
| 4,425,545 | 1/1984 | Scalese | 324/202 |
| 4,453,408 | 6/1984 | Clayman | 73/1 DV |
| 4,462,082 | 7/1984 | Thiele et al. | 73/1 DV X |
| 4,466,270 | 8/1984 | Kimura et al. | 73/1 DV X |
| 4,565,974 | 8/1984 | Sparks | 324/202 |

FOREIGN PATENT DOCUMENTS

| | | | |
|---|---|---|---|
| 84989 | 8/1983 | European Pat. Off. | 73/1 DV |
| 2814336 | 5/1979 | Fed. Rep. of Germany | 73/1 DV |
| 2852752 | 7/1979 | Fed. Rep. of Germany | 73/1 DV |
| 87810 | 7/1981 | Japan | 378/207 |
| 431434 | 6/1974 | U.S.S.R. | 378/207 |
| 462127 | 7/1975 | U.S.S.R. | 73/1 DV |
| 1018001 | 5/1983 | U.S.S.R. | 324/202 |

OTHER PUBLICATIONS

"Ultrasonic Weld Inspection Using Rectangularcalibration Screen Overlays"; *Materials Evaluation;* vol. 40, No. 10, pp. 1068–1070; Sep. 1982; W. S. Burke.

*Primary Examiner*—Tom Noland
*Attorney, Agent, or Firm*—Handal & Morofsky

[57] ABSTRACT

The control specimen according to the invention consists of a metal basic body and artificial inclusions arranged in it, where the inclusions are suitably sintered, non-metallic configurations arranged according to size and distribution conforming to the purpose of the test. During production of the control specimens at least one layer is formed with metal melt, into which inclusion, inclusions is/are inserted conforming to the shape and arrangement of the required fault location or locations. It is practicable to form at least one further upper layer from the metal melt inclusions. Further inclusions may be arranged in the top layer and in given case further top layers are formed with or without inclusions. The artificial defects can be produced either by forming cavities into the layer after solidification and cooling, and inserting the inclusion(s) into the appropriate cavity or cavities, or spreading them into the layer-forming metal melt before solidification.

18 Claims, 8 Drawing Figures

|    | A       | B        | C        | D        | E   |
|----|---------|----------|----------|----------|-----|
| 1  | Gø3     | L5×15    | H9.6×14  | Gø3      | Gø3 |
| 2  | Gø7     | H3.2×7   | Gø4      | Gø5      | Gø5 |
| 3  | L5×5    | H4.2×12  | Gø3      | Gø7      | Gø3 |
| 4  | Gø3     | L5×10    | H3.9×7   | Gø3      | Gø3 |
| 5  | Gø7     | L5×15    | H5.4×15  | Gø5      | Gø5 |
| 6  | L5×5    | L10×25   | H9.6×14  | Gø7      | Gø3 |
| 7  | Gø3     | Gø7      | L10×10   | H3.2×7   | Gø3 |
| 8  | Gø5     | L5×5     | L10×25   | H4.2×12  | Gø5 |
| 9  | Gø9     | L5×10    | L5×15    | H5.4×15  | Gø3 |
| 10 | Gø5     | L10×10   | H5.8×10  | Gø6      | Gø3 |
| 11 | Gø9     | H5×10    | Gø4      | Gø4      | Gø9 |
| 12 | Gø5     | L10×10   | H5.8×10  | Gø6      | Gø3 |
| 13 | Gø9     | L10×25   | Gø6      | Gø8      | Gø9 |
| 14 | L5×10   | H5.4×15  | Gø8      | Gø8      | Gø8 |

G = SPHERE ø

H = CYLINDER (ø × LENGTH)

L = TIP (LENGTH × WIDTH × THICKNESS)

Fig. 7

CONTROL SPECIMEN FOR EVALUATION OF NON-DESTRUCTIVE TEST RESULTS, ARTIFICIAL INCLUSIONS AND PROCESS FOR PRODUCING CONTROL SPECIMENS

FIELD AND BACKGROUND OF THE INVENTION

The invention relates to a control specimen for evaluation of non-destructive test results and for the comparison of results measured on metal work piece vs. results measured on the control specimen, furthermore for the production of artificial inclusions used in control specimens, and a process for producing said control specimens.

The propagation and development of the ultrasonic method are most dynamic among the non-destructive test methods used for checking the internal structural imperfections of joints and parts made of metal. Apart from the numerous economic and technical benefits of its applicability, it is indisputable that interpretation of the ultrasonic signals received during testings and the evaluation referring to the character and magnitude of the defects detected in the joint generally lag behind the qualitative requirement level demanded by the designers.

In the course of checking by radiographic method, the defects of the material appear in projection, where determination of the extension of the imperfections represents uncertainty. In order to reduce the shortcomings of the evaluation in the non-destructive methods and to reproduce the test results, various methods have been developed and each can be traced back to the application of of certain standard type.

The control specimens presently used for ultrasonic testing of joints are divided into three groups:
- internationally recognized, standardized control specimens, made of highly reliable, unalloyed steel, the geometry of which is independent from the purpose of the test,
- individual, welded control specimens, the formation of which is somehow connected with the test piece (material, surface, geometry, etc).
- individual control specimens without welding, the thickness, material and surface quality of which are similar to those of the test piece.

Use of the three standard type can be traced back to the same principle, i.e. that the signals received on the oscilloscope with the aid of reference surfaces formed on the control specimen (rear wall, bottom hole perpendicular to the ultrasonic beam of rays, hole perpendicular to and parallel with the tested surface) can be compared with the signals received during the tests on basis of the amplitudes. The comparison serves for determination of the testing technology (gemetric and sensitivity calibrations) and for reproduction of the results. The indices obtained from the use of standard types refer only to the signal magnitudes received from the reference surfaces, and do not give any direct connection for determination of the actual extent and character of the faults. Identical signal levels—depending on the location, fault type, orientation—may represent 200–300% dimensional difference. Accordingly, conversion of the ultrasonic test results is presently unsolved for the designer's requirements in respect of the actual size of the imperfect joint.

Ultrasonic holography is a very expensive laboratory procedure, which increases the accuracy of fault estimation with the aid of an oscillator having an electronically variable sound space.

SUMMARY AND OBJECTS OF THE INVENTION

Thus the object of the present invention is to provide control specimens which allow the deliberate and planned realization of different inclusion in the material, and their reproducible comparison with the defects of the work pieces.

A further object of the invention is to provide artificial inclusions whereby optional control specimens or set of control specimens can be produced, and the material and shape of which are nearly identical with those of the actual imperfections during testing.

Another object of the present invention is to provide a method for producing control specimens from different artificial inclusions elements.

According to the invention, the control specimens are made of a metal basic body in which artificial inclusion elements are arranged. The inclusions are suitably sintered, heat treated non-metallic configurations, preferably spherical, cylindrical and tipped or irregular bodies arranged in the control specimen according to the size and distribution suited to the use of the work piece or purpose of the test.

The inclusions may be corundum- or carbide-based materials.

Composition of the corundum-based material may be the following:

| Composition | density /g/cm$^3$/ | hardness /HRA/ |
|---|---|---|
| Al$_2$O$_3$ min. 99%<br>NaO max. 0.5%<br>Fe$_2$O$_3$ max. 0.4%<br>SiO$_2$ max. 0.1% | 3–4 | 80–90 |

The carbide-based material may be produced from carbides or from their optional combination:

| Type of carbide | density /g/cm$^3$/ | hardness /HV/ |
|---|---|---|
| W$_2$C | 17.15 ± 5% | 3000 ± 10% |
| WC | 15.52 ± 5% | 2200 ± 10% |
| TiC | 4.23 ± 5% | 3000 ± 10% |
| TaC | 14.49 ± 5% | 1800 ± 10% |
| Cr$_2$C$_2$ | 6.68 ± 5% | 1500 ± 10% |
| VC | 5.36 ± 5% | 2100 ± 10% |

The inclusions are suitably spherical, cylindrical or tipped bodies, but in given case they may be of other, e.g. irregular shapes.

The control specimens according to the invention can be produced from at least one layer of metal melt in which inclusion element or elements are arranged conforming to the shape and arrangement of the fault locations. It is advisable to form at least a further upper layer with the metal salt, whereby the inclusion is covered.

The inclusion element of elements can be arranged by forming cavities in the layers after solidification and cooling and inserting the inclusion(s) into the cavity or cavities. The inclusion elements can be arranged in the non-solidified layer as well. In certain cases the elements can be arranged still before preparation of the layer, when they are suitably fixed to prevent their dislocation by the metal melt.

If the inclusions are arranged in cavities, then these and the layer surface must be cleaned prior to and/or after insertion.

The layers forming the control specimens can be prepared by melting and casting or welding.

The control specimens according to the invention can be optionally shaped, and they may contain one or several systematically arranged artificial inclusions. Since the ultrasonic energy conductivity, feed back capacity and the radiographically appreciable radiation absorbability of the artificial inclusions are identical with the indices of the real non-metallic inclusions, the control specimens according to the invention considerably increase the signal interpretation possibilities of the ultrasonic and radiographic tests.

If the inclusions are arranged before formation or solidification of the layers, it may be practicable to produce such elements the specific weight of which is at least the same as that of the metal melt, or suitably heavier in order that the inclusions should not remain in the uppermost part of the layer. This can be suitably realized if the inclusions contain heavier, preferably metallic core.

The invention is based on the recognition, that arrangement of the artificial inclusion conforming to the type, size and arrangement of the defects occurring during the test (e.g. surface fault, distance between faults, etc.) represents such basis of comparison for checking the requirements of the non-destructive test, which was not possible so far.

The standard piece produced according to the process may be part of the test piece designated for this purpose.

In view of the foregoing, one of the fundamental fields of application of the standard piece is determination of the accurate dimension and character of the faults in the joint.

BRIEF DESCRIPTION OF THE DRAWINGS

Further details of the invention are described by way of examples, with the aid of the drawings in which.

DESCRIPTION OF THE PREFERRED EMBODIMENTS

Figure 1:
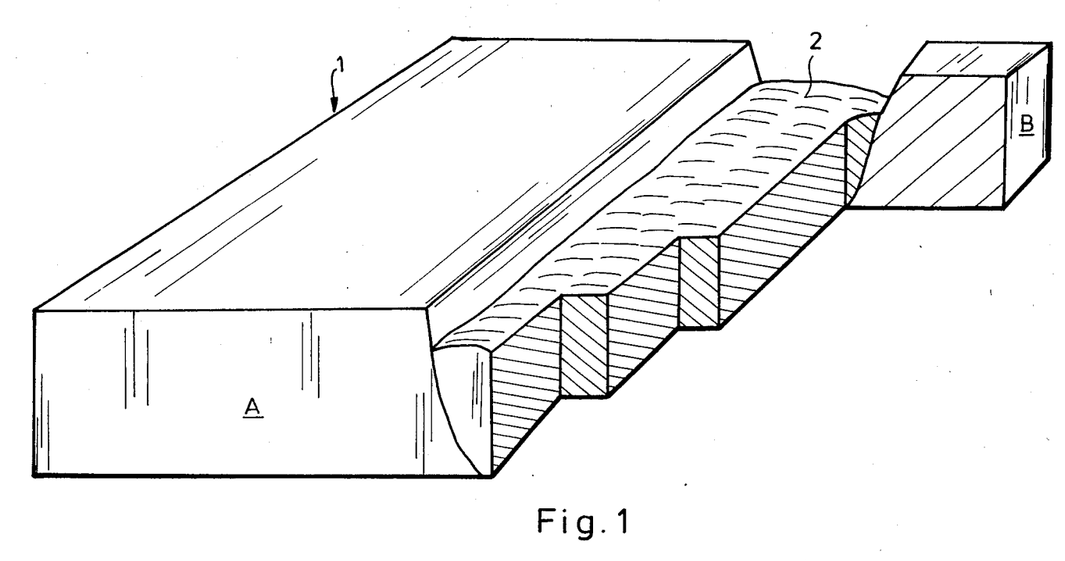
FIG. 1 is the first phase of the production of a control specimen used for butt weld.

FIG. 1 shows a control specimen 1 of 62 C type steel consisting of faces A and B. The opposite edges of faces A and B are machined at an angle, thus—arranged side by side—they are suitable for V-shaped butt joint. The diagram shows the first layer of the joint 2. The joint 2 was prepared by submerged arc welding, when S2 type electrode and 10.42 type flux were used.

Figure 2:
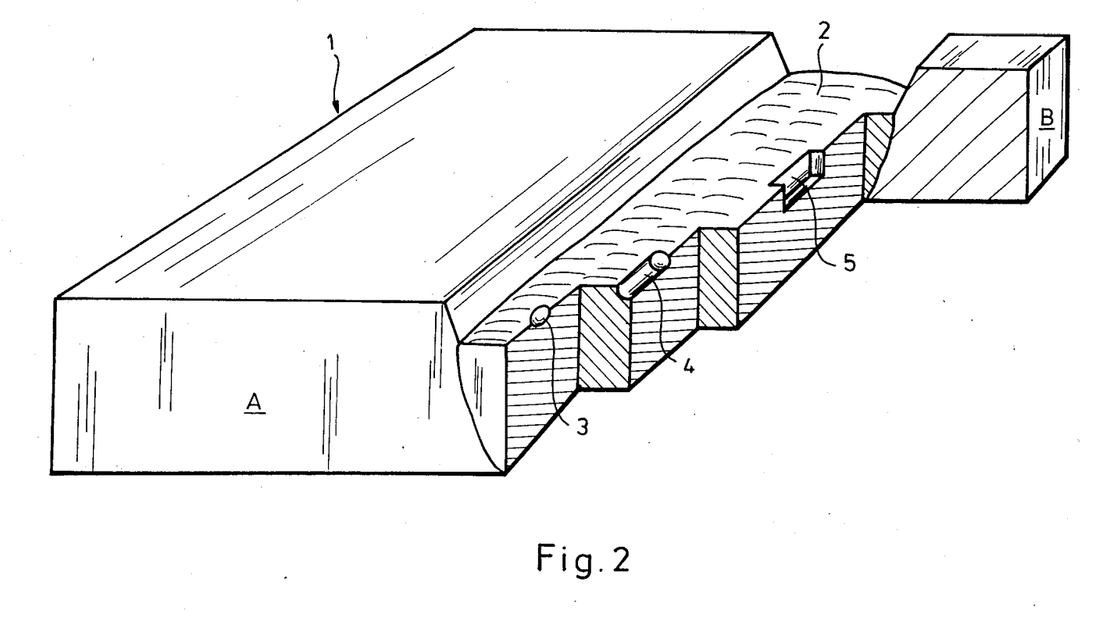
FIG. 2 is the second phase of the production.

FIG. 2 shows cavities 3,4 and 5 machined in the finished part of joint 2. Cavity 3 is spherical, cavity 4 cylindrical and cavity 5 is tipped. The cavities 3, 4 and 5 are shaped as to keep the upper point of the spherical, cylindrical and tipped inclusions inserted therein at least at the height of the surfaces of joint 2, suitably minimally above it.

Figure 3:
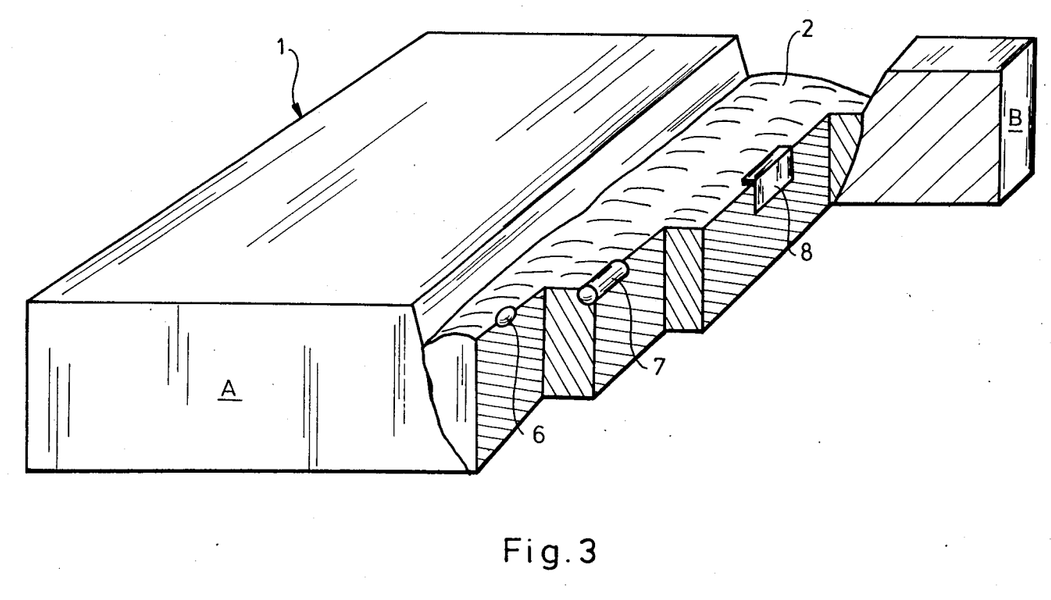
FIG. 3 is the third phase of the production.

FIG. 3 shows the arrangement of artificial inclusions 6, 7 and 8 in cavities 3, 4 and 5. The inclusions 6 is tipped. As seen, the upper part minimally extend from the surface of joint 2. This is practicable to prevent the formation of air bubble between the weld layer and surface of the artificial inclusions 6, 7 and 8.

Figure 4:
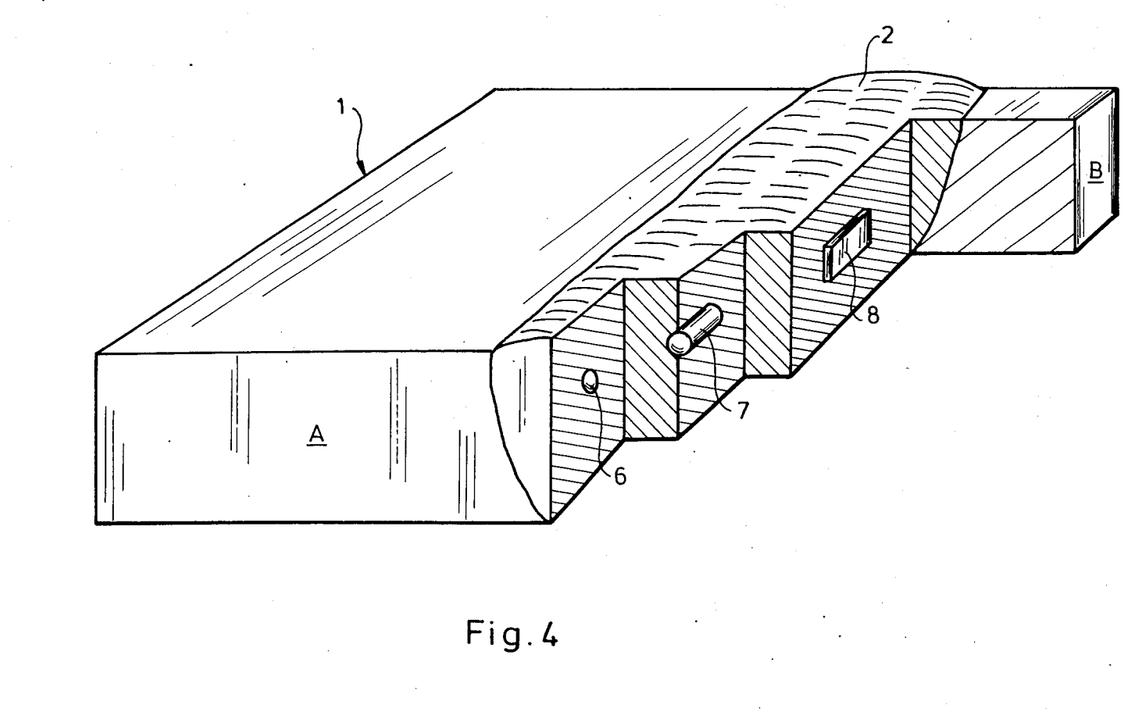
FIG. 4 is the final phase of the production.

FIG. 4 shows the sectional view of the finished control specimen 1 with the artificial inclusions 6, 7 and 8 arranged in joint 2.

Figure 5:
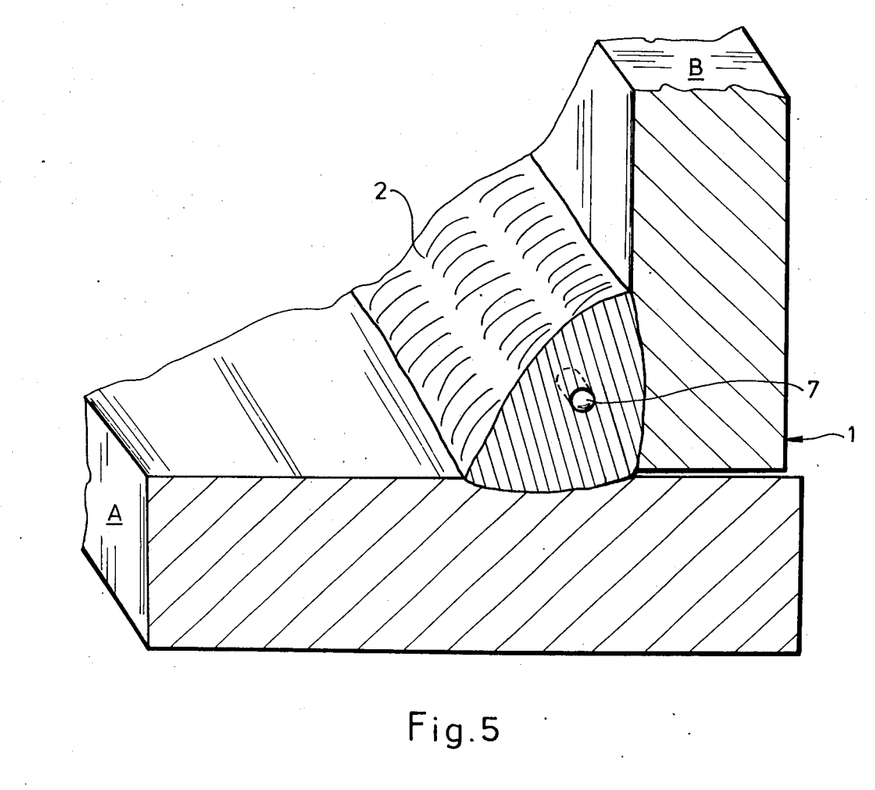
FIG. 5 is the sectional view of the control specimen in case of corner weld.

Naturally the control specimen can be produced similarly in other formation too. In FIG. 5 for example the control specimen 1 was made of KL2 material and faces A and B surround corner weld prepared by EB12 electrode and arc welding, in which the artificial inclusions are arranged. The section shows the end part of a cylindrical inclusion 7.

Figure 6:
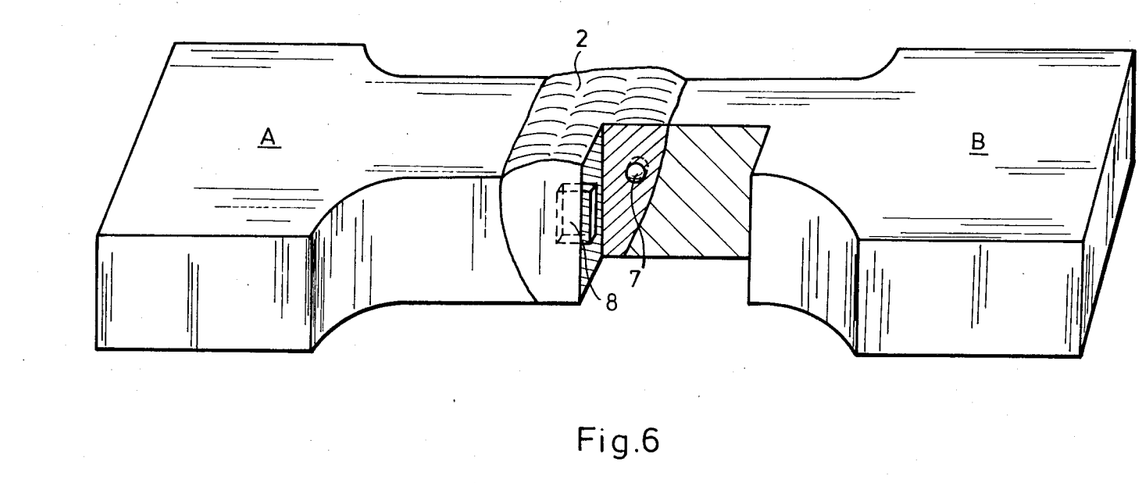
FIG. 6 is the sectional view in part of the control specimen produced as tensile test piece.

Test piece too can be produced according to the invention. This is shown in FIG. 6, and it consists of faces A and B connected by joint 2. The inclusions 7 and 8 are arranged in joint 2. The middle part of the test piece is provided with the usual neck part.

Figure 6A:
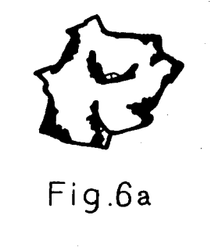
FIG. 6a illustrates an irregularly shaped inclusion.

FIG. 6a shows an inclusion which is of irregular shape.

Figure 7:
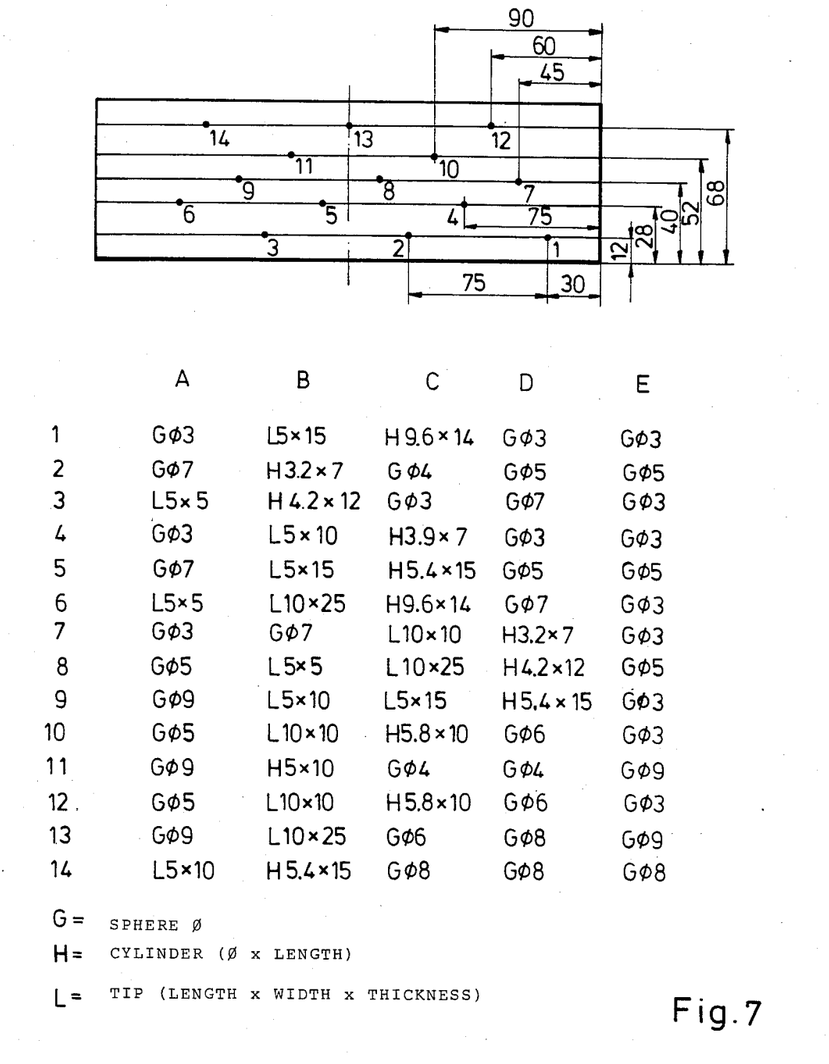
FIG. 7 is the sectional view of an alternative shape of the control specimen along the median plane of the joint.

FIG. 7 shows the sectional view of the joint of a systematically prepared control specimen with the fault locations 1-14 arranged in the various layers of the joint. Arrangement of the fault locations (1 to 14) is shown in the section, and the type and size of the artificial inclusions (G,H,L) and are shown in the Table below the section for five different test pieces (A to E).

In other words the table of FIG. 7 contains five examples (A to E). Each example shows which of the artificial inclusions are arranged at the various points (1 to 14) of the cross section shown in the distribution arrangement above the table in FIG. 7.

The notation used in FIG. 7 represent the following:

G means a sphere with a diameter ($\phi$) indicated in the table;

H means a cylinder and the data associated with the letter H in the table are diameters and length;

L means a plate, wherein length and width are indicated in the table. The thickness of all plates is constant.

This type of complex control specimen is suitable for the conduction of several tests.

The inclusions shown in FIGS. 1-4 consist of a sintered alloy containing 99.5% corundum, 0.26% sodium oxide, 0.2% $Fe_2O_3$ and 0.04% silicium oxide. These are produced with the well-known technology: the alloy produced in powdery mixture is moulded by pressing, followed by heating at 1500°–1700° C. temperature. Density of the so-obtained inclusions is 3–4 g/cm$^3$, hardness 80–90 HRA.

Naturally the artificial inclusion may be produced from other alloys too, e.g. from carbide. Tungsten carbide, titanium carbide, chromium carbide or vanadium carbide are applicable in optional combination for this purpose. The inclusion shown in FIGS. 5 and 6 consist of 40% $W_2C$, 40% TiC and 20% TaC. The inclusions are produced with the well-known sintering technology also in this case.

The convenient dimension range of the exemplary inclusions in case of a spherical or irregular shape is 1–15 mm diameter, in case of a cylindrical shape 1–15 mm diameter and 1–10 mm long, and in case of a tipped shape 2×2×1 mm through 40×40×5 mm. The tipped shape means a rectangular brick-like body (parallelepiped) with the dimensional ranges of its edges as mentioned.

The control specimens can be produced by welding or casting. If the control specimens are produced by welding, preparation of the welding does not require special procedure, it is basically the same as the technology of the joint preparation of work piece.

The artificial inclusions are arranged in such a manner, that they are surrounded by weld metal inserted into the weld layer corresponding to the intended depth of the defect. Welding of the elements is followed by finishing the welding of the weld layer.

Though the artificial inclusions in the examples are arranged in cavities machined in the solidified layers, obviously this is not the only solution for the arrangement. The technology may be simplified by insertion of the inclusions directly into the metal melt, prior to, during or directly after formation of the melt layer. Since however the material of the inclusions is usually lighter than the material of the melt, the inclusions spread into the melt float on the surface of the metal bath. In this case it is practicable to prepare such elements, the specific weight of which is at least identical with that of the melt. This is solved by placing such metallic core into the artificial inclusions, which ensures the appropriate weight thereof. The thickness of the material surrounding the core is sufficient in any case to identify the inclusion as inclusion during the test.

In given case the inclusions according to the invention can be fixed. This is essential first of all when the artificial inclusions are arranged before preparation of the melt layer. The fixing may be carried out by metal wire of high melting point, magnet or by other method.

The material of the control specimen is to be checked by ultrasonic method before welding. The qualitative specification for the material of the work piece is valid for the material of control specimen. The welding joint is tested layer by layer with radiographic method. Purpose of the test is to realize the control specimen by checking the sound condition of the artificial inclusions and to maintain the permanent internal faultless condition of the joint by checking the other parts of the joint. In case of damaged artificial inclusions or natural fault in the joint, it is to be repaired according to the technology given for the original work piece.

The joint of the finished control specimen is checked by ultrasonic procedure.

Use of the control specimen with the known size, arrangement and type of the artificial inclusions increases the reliable checking of the joint.

Direct connection can be established between the result of the non-destructive test (ultrasonic signal group blackening of fault, etc.) and the extent of the fault.

The complementary use of the non-destructive testing methods can be reduced. The use of the generally required expensive radiographic method for complementing the ultrasonic test can be considerably reduced, or occasionally dispensed with.

Where radiographic tests can not be conducted at all, or only within limits (e.g. in each of periodical tests on the primary circuit of atomic power plant), the economic damages arising from the uncertain interpretation of the ultrasonic test results may be substantial, since extending the length of off-time, unjustifiable repairs are extremely costly.

The process is applicable for both manual and mechanical ultrasonic testing of the joint. The theory of the ultrasonic tests may be promoted by the fact that instead of the indices not showing any direct connection with the joint imperfections, the reflexibility of real defects can be considered as a basis for comparison of the testing signal groups.

The artificial inclusions can be arranged in the joints also which are designated for testing. Following the calibration of the sensitivity of the ultrasonic or radiographic checking, the imperfect parts can be removed.

The requirement system related to the internal faults of the material of the radiographic or other (eddy-current, magnetic) testing is similarly realizable with the control specimens according to the invention.

Furthermore the method according to the invention is suitable for the development of the signal interpretation of ultrasonic and radiographic tests and optimal testing technology.

What we claim is:

1. A control specimen for evaluation of non-destructive test results and for comparison of results measured on metal work pieces vs. the results measured on the control specimens, said control specimen consisting of a metal basic body and at least one artificial inclusion arranged in it, said inclusions are sintered non-metallic configuration, and are arranged according to the size and distribution conforming to the utilization of the work piece and to the purpose of the test, and wherein the composition of said at least one inclusion is as follows:

$A_2O_3$: min. 99%,
NaO: max. 0.5%,
$Fe_2O_3$: max. 0.4%,
$SiO_2$: max. 0.1%.

2. The control specimen as claimed in claim 1, characterized in that the hardness of said at least one artificial inclusion is 80–90 HRA.

3. The control specimen as claimed in claim 1, characterized in that the density of said at least one artificial inclusion is 3–4 $g/cm^3$.

4. The control specimen as claimed in claim 1, characterized in that said at least one artificial inclusion is spherical.

5. The control specimen as claimed in claim 1, characterized in that said at least one artificial inclusion is cylindrical.

6. The control specimen as claimed in claim 1, characterized in that said at least one artificial inclusion is tipped.

7. The control specimen as claimed in claim 1, characterized in that said at least one artificial inclusion is of irregular shape.

8. A process for the production of control specimen as claimed in claim 1, characterized in that at least one layer is formed with metal melt in which said at least one artificial inclusion is arranged conforming to the shape and arrangement of the required fault location or locations.

9. The process as claimed in claim 8, characterized in that at least one further upper layer is formed with melt to cover said at least one artificial inclusion.

10. The process as claimed in claim 9, characterized in that inclusions are arranged also in said upper layer and in that further upper layers are formed.

11. The process as claimed in claim 8, characterized in that said at least one artificial inclusion is inserted into a cavity formed in the layer after solidification and cooling.

12. The process as claimed in claim 11, characterized in that prior to insertion of the said at least one artificial inclusion, the surface of the layer and of the cavity is cleaned.

13. Process as claimed in claim 11, characterized in that after insertion of said at least one artificial inclusion, the surface of the layer and of the cavity is cleaned.

14. The process as claimed in claim 8, characterized in that said at least one artificial inclusion is arranged by spreading into the layer-forming metal melt before solidification and cooling.

15. The process as claimed in claim 14, characterized in that said at least one artificial inclusion is arranged before preparation of the layer.

16. The process as claimed in claim 15, characterized in that said at least one artificial inclusion is fixed before preparation of the layer.

17. The process as claimed in claim 8, characterized in that said at least one layer is prepared by melting and casting.

18. The process as claimed in claim 8, characterized in that said at least one layer is prepared by welding.

* * * * *